US012682498B2

(12) United States Patent
Charles

(10) Patent No.: US 12,682,498 B2
(45) Date of Patent: Jul. 14, 2026

(54) COLOR CORRECTION IN OPHTHALMIC IMAGING

(71) Applicant: Alcon Inc., Fribourg (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 327 days.

(21) Appl. No.: 18/358,882

(22) Filed: Jul. 25, 2023

(65) Prior Publication Data

US 2024/0037794 A1 Feb. 1, 2024

Related U.S. Application Data

(60) Provisional application No. 63/394,113, filed on Aug. 1, 2022.

(51) Int. Cl.
*G06T 7/90* (2017.01)
*A61B 3/117* (2006.01)
(Continued)

(52) U.S. Cl.
CPC .............. *G06T 7/90* (2017.01); *A61B 3/1176* (2013.01); *G06T 7/0012* (2013.01); *G06T 7/73* (2017.01);
(Continued)

(58) Field of Classification Search
CPC G06T 7/90; G06T 7/00; G06T 7/0012; G06T 7/73; G06T 2200/24; G06T 2207/30041;
A61B 3/117; A61B 3/1176; A61B 3/12; A61B 3/13; A61B 3/00; A61B 3/0025; G06V 40/18; G06V 40/197; G16H 30/40
See application file for complete search history.

(56) References Cited

U.S. PATENT DOCUMENTS 7,147,328 B2 * 12/2006 Sugino ..................... A61B 3/14
351/200
8,905,544 B2 * 12/2014 Shimizu ................. A61B 3/117
351/205
(Continued)

FOREIGN PATENT DOCUMENTS

CN 102421352 A * 4/2012 .......... A61B 3/0025
CN 107543503 A * 1/2018 ............ G01B 11/06
(Continued)

*Primary Examiner* — Stephen R Koziol
*Assistant Examiner* — Benedict E Lee

(57) ABSTRACT

Certain embodiments provide a method of generating a color-corrected ophthalmic image. The method comprises obtaining an ophthalmic image of an eye with a nuclear sclerotic cataract or a tinted intraocular lens ("IOL"). The method further comprises determining color-shift information associated with the ophthalmic image based on at least one of user input and by processing the obtained image, the color-shift information indicative of the extent to which color in the obtained image is to be corrected to at least partially remedy the effect of the nuclear sclerotic cataract or the tinted IOL on the color of the obtained image. The method further comprises color-correcting the ophthalmic image based on the color-shift information. The method further comprises generating the color-corrected ophthalmic image based on the color-correcting.

14 Claims, 2 Drawing Sheets

(51) Int. Cl.

| | | |
|---|---|---|
| *G06T 7/00* | (2017.01) |
| *G06T 7/73* | (2017.01) |
| *G06V 40/18* | (2022.01) |
| *G16H 30/40* | (2018.01) |

(52) U.S. Cl.
CPC .......... *G06V 40/197* (2022.01); *G16H 30/40* (2018.01); *G06T 2200/24* (2013.01); *G06T 2207/30041* (2013.01)

(56) References Cited

U.S. PATENT DOCUMENTS

| | | | |
|---|---|---|---|
| 9,750,402 B2 * | 9/2017 | Ono ..................... A61B 3/0025 |
| 10,849,789 B2 * | 12/2020 | Dewey ................... A61B 3/103 |
| 11,156,835 B2 * | 10/2021 | Samec ............... G02B 27/0172 |
| 12,336,762 B2 * | 6/2025 | Sisson ..................... A61B 3/14 |
| 2004/0004694 A1 | 1/2004 | Sugino et al. |
| 2008/0221674 A1 * | 9/2008 | Blum ...................... G02C 7/04 |
| | | | 623/5.11 |

| | | | |
|---|---|---|---|
| 2013/0003016 A1 * | 1/2013 | Feldon ..................... A61B 3/14 |
| | | | 351/246 |
| 2014/0125949 A1 * | 5/2014 | Shea ................... A61B 3/1035 |
| | | | 351/205 |
| 2016/0220108 A1 | 8/2016 | Ono |
| 2017/0273781 A1 * | 9/2017 | Zhao ..................... A61F 2/1645 |
| 2018/0153403 A1 * | 6/2018 | Suzuki ................... A61B 3/117 |
| 2022/0115122 A1 * | 4/2022 | Enoki ................... G16H 30/40 |
| 2022/0148179 A1 * | 5/2022 | Takeuchi ................. G01J 3/50 |
| 2023/0084284 A1 * | 3/2023 | Burwinkel ........... G06T 7/0012 |
| | | | 382/131 |
| 2023/0410306 A1 * | 12/2023 | Anderson ............. A61B 3/152 |

FOREIGN PATENT DOCUMENTS

| | | | | |
|---|---|---|---|---|
| CN | 109009658 B | * | 3/2021 | ............. A61B 3/107 |
| JP | 2005131066 A | | 5/2005 |
| JP | 2008284005 A | | 11/2008 |
| WO | WO-2008067109 A1 | * | 6/2008 | ............. G02C 7/104 |
| WO | WO-2018021561 A1 | * | 2/2018 | .......... A61B 3/0025 |
| WO | WO-2022013794 A1 | * | 1/2022 | ............... G06T 5/00 |

* cited by examiner

OBTAIN AN
OPHTHALMIC IMAGE — 210

DETERMINE COLOR-SHIFT
INFORMATION ASSOCIATED WITH THE
OPHTHALMIC IMAGE — 220

AUTOMATICALLY COLOR-CORRECT
THE OPHTHALMIC IMAGE BASED ON
THE COLOR-SHIFT INFORMATION — 230

GENERATE A COLOR CORRECTED
OPHTHALMIC IMAGE — 240

COLOR CORRECTION IN OPHTHALMIC IMAGING

BACKGROUND

During ophthalmic screenings, such as a retina screening, practitioners must be able to clearly view or capture clear and accurate images of the eye for proper diagnosis, preferably with minimal discomfort or invasiveness to patients. To do so, practitioners may view the eye using various visualization devices (e.g., indirect ophthalmoscope, 28-30 diopter lens, or a slit-lamp with 78-90 diopter lens) or various types of specialized imaging devices that produce digital retinal imaging, multi-spectral imaging, or high-spectral imaging. Retinal screening is typically performed to diagnose retinal diseases, such as age-related macular degeneration (AMD), nuclear sclerotic cataract, diabetic retinopathy, hypertensive retinopathy, etc.

However, whether viewed through a visualization device or as a digital image, the color appearance of the vitreous and the retina may be altered in the presence of a nuclear sclerotic cataract, a yellow tinted intraocular lens ("IOL"), or for some other reason. For example, white lesions may appear yellow because of the yellowish color of a nuclear sclerotic cataract or a yellow tinted IOL. Such yellowing can make it more difficult to determine, for example, geographic atrophy for diagnosis of dry macular degeneration in a patient. Further, the yellowing can make it more difficult to accurately determine a level, degree, or severity of the dry macular degeneration condition. Discoloration of the vitreous and the retina may also potentially confuse artificial intelligence or digital image systems into making errors.

BRIEF SUMMARY

The present disclosure relates generally to systems and methods for color-correcting an ophthalmic image.

Certain embodiments provide a method of generating a color-corrected ophthalmic image. The method comprises obtaining an ophthalmic image of an eye with a nuclear sclerotic cataract or a tinted intraocular lens ("IOL"). The method further comprises determining color-shift information associated with the ophthalmic image based on at least one of user input and by processing the obtained image, the color-shift information indicative of an extent to which color in the obtained image is to be corrected to at least partially remedy an effect of the nuclear sclerotic cataract or the tinted IOL on the color of the obtained image. The method further comprises color-correcting the ophthalmic image based on the color-shift information. The method further comprises generating the color-corrected ophthalmic image based on the color-correcting.

Certain embodiments provide an ophthalmic imaging system comprising an imager configured to obtain an ophthalmic image of an eye with a nuclear sclerotic cataract or a tinted intraocular lens ("IOL"). The ophthalmic imaging system further comprises one or more memories configured to store executable instructions as well as one or more processors in data communication with the one or more memories. The one or more processors are configured to execute the instructions to determine color-shift information associated with the ophthalmic image based on at least one of user input and by processing the obtained image, the color-shift information indicative of an extent to which color in the obtained image is to be corrected to at least partially remedy an effect of the nuclear sclerotic cataract or the tinted IOL on the color of the obtained image. The one or more processers are further configured to execute the instructions to color-correct the ophthalmic image based on the color-shift information. The one or more processors are configured to execute the instructions to generate the color-corrected ophthalmic image based on the color-correcting.

The following description and the related drawings set forth in detail certain illustrative features of one or more embodiments.

BRIEF DESCRIPTION OF THE DRAWINGS

The drawings described herein are for illustrative purposes only, are schematic in nature, and are intended to be exemplary rather than to limit the scope of the disclosure.

Figure 1:
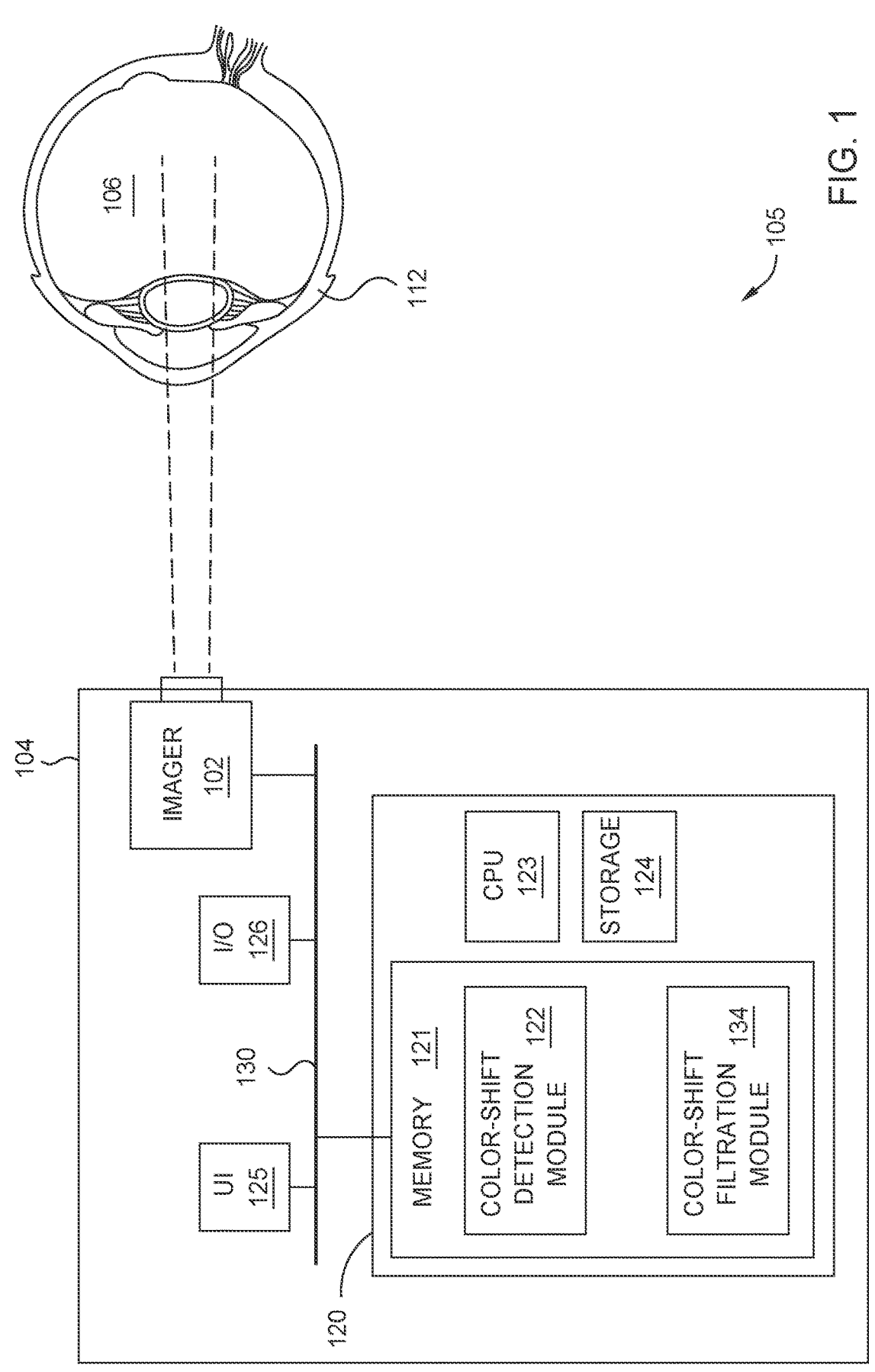
FIG. 1 shows a diagram of an example ophthalmic environment including an imaging device and a patient's eye, according to certain embodiments.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

Implementations of color correction in ophthalmic imaging disclosed herein may overcome some or all of the challenges described above by generating a color corrected digital image having reduced or eliminated color-shift as compared to a raw image of the vitreous and the retina captured, for example, during an ophthalmic screening. In certain embodiments, the color corrected digital image is generated by applying a filter to the raw image, thereby reducing the color-shift. A color-shift in an image refers to the color of the image or various structures (e.g., anatomical objects, tissues, proteins, cells, etc.) or portions therein being different than the expected (e.g., true or natural) color of such structures or portions in the image.

In certain embodiments, the filter is applied to a raw image based on or in response to color-shift information, which can include information that is input via a user interface (UI) and/or information that is automatically determined from the raw image. For example, in certain embodiments, a practitioner may provide input via a UI indicating that the patient's eye has a nuclear sclerotic cataract or a yellow-tinted IOL. In another example, images including structures having a known color can have associated color-shift information determined by measuring a difference between the known color of the structure and the corresponding color of the structure as it appears in the raw image, which may have been color-shifted. For example, in certain embodiments, an optic nerve head present in the raw image is used as a reference. The optic nerve head has a white natural color, but may appear yellowed due to the presence of a nuclear sclerotic cataract or a yellow-tinted IOL. In such an example, color-shift information can be automatically determined by measuring the difference between a color of the optic nerve head as shown in the raw image and the color white (or of a natural color of the optic nerve head, which may be white). In certain embodiments, instead of or in addition to using the optic nerve head as a reference, the oxyhemoglobin and/or deoxyhemoglobin within retinal arteries and veins may act as a reference. Oxyhemoglobin is typically red or bright red and deoxyhemoglobin is bluish-purple. However, the color of oxyhemoglobin and deoxyhemoglobin may appear differently in an image due to the presence of a nuclear sclerotic cataract or a yellow-tinted IOL. As such, color-shift information can be automatically determined by measuring the difference between a color of the oxyhemoglobin and/or deoxyhemoglobin within retinal arteries and veins as shown in the raw image and the natural color of oxyhemoglobin and/or deoxyhemoglobin.

In various embodiments, reference may be made to yellowing, yellow-shift, etc., due to cataracts or certain IOLs causing yellowing of raw multispectral images. Although yellowing is exemplified in various embodiments, it will be appreciated that various aspects disclosed are not thus limited and may be suitable for reducing any kind of color-shift in ophthalmic imaging.

FIG. 1 illustrates a diagram of an example ophthalmic environment 105 showing an ophthalmic imaging device 104 for capturing images of a patient's eye 106. For example, ophthalmic environment 105 may correspond to an ophthalmic screening environment in a screening room where a screening procedure is being performed to screen for macular degeneration. In such an example, a screener or practitioner may use imaging device 104 to capture images of the patient's vitreous and/or retina.

According to various embodiments, the imaging device 104 may be a digital imaging device, a multi-spectral imaging device, or a hyper-spectral imaging device, or any other ophthalmic imaging device capable of performing ophthalmic imaging, etc. As shown, the imaging device 104 comprises an imager 102, a controller 120, a user interface 125, an interconnect 130, and an I/O device interface 126, which may allow for the connection of various I/O devices to viewing device 104.

Imager 102 may be any imager, imaging component, or imaging device known to one of ordinary skill in the art for capturing ophthalmic images. For example, imager 102 may be a digital imager, such as a digital camera, for capturing images of various optical components of the eye, such as the vitreous and the retina. In the embodiments of FIG. 1, imager 102 may be integrally formed with the imaging device 104 and controlled by the controller 120. In other embodiments, however, imager 102 and imaging device 104 may be separate devices, in which case, imager 102 may be controlled by the controller 120 instead via wired or wireless connection.

The controller 120 includes a central processing unit (CPU) 123, a memory 121, and a storage 124. CPU 123 may retrieve and execute programming instructions stored in memory 121. Similarly, CPU 123 may retrieve and store application data residing in memory 121. The interconnect 130 transmits programming instructions and application data, among CPU 123, I/O device interface 126, user interface 125, memory 121, the storage 124, etc. CPU 123 can represent a single CPU, multiple CPUs, a single CPU having multiple processing cores, and the like. Additionally, in certain embodiments, the memory 121 represents volatile memory, such as random access memory (RAM). Furthermore, in certain embodiments, storage 124 may be non-volatile memory, such as a disk drive, solid state drive, or a collection of storage devices distributed across multiple storage systems.

As shown, memory 121 includes a color-shift detection module 122 and a color-shift filtration module 134. The color-shift detection module 122 refers to an application or set of software instructions for detecting a color-shift present in raw images captured by the imager 102. In certain embodiments, the color shift detection module 122 may detect a color shift based on color-shift information provided by user input. For example, as further described below, a practitioner may provide input indicating that the patient has a nuclear sclerotic cataract or a yellow-tinted IOL. Using the color-shift information provided by such user input, the color shift detection module 122 is configured to detect the presence of a color-shift in a raw image captured from the patient's eye.

The color shift detection module 122 may, alternatively or additionally, detect a color-shift by processing and analyzing the raw image. For example, in certain embodiments, the color shift detection module 122 may detect a color-shift by processing the raw image, identifying a structure in the raw image, and determining color shift information associated with the raw image based on a difference between the color of the structure as captured in the image and the actual color of the structure. The actual color of a structure refers to the structure's natural color, which is consistent across all patients regardless of any ophthalmic conditions or diseases. As described in further detail below, an example of a structure that can be used as a reference in the embodiments described above is the optic nerve head, which is always white. Other reference structures, as described above, include oxyhemoglobin and deoxyhemoglobin in retinal arteries and veins.

The color-shift filtration module 134 may be configured to color correct a raw image captured by imager 102. A variety of techniques known to one of ordinary skill in the art may be used for automatically color correcting a raw image based on the color-shift information input by a user and/or automatically derived from a raw image. Color-shift information input by a user may indicate one or more of: a color of the patient's nuclear sclerotic cataract, the type and/or color of an IOL, etc., as described below. Color-shift information derived automatically by processing a raw image may indicate the intensity values (e.g., red, green, blue (RGB) values) associated with one or more pixels in the raw image. Based on the color-shift information, the color-shift filtration module 134 is configured to adjust the RGB values of one or more pixels in the raw image in order to achieve desired RGB values for each of the one or more pixels. For example, in certain embodiments, the color-shift filtration module 134 may generate and apply a color compensation or correction filter to the raw image, where the filter is representative of an offset in RGB values for each pixel in the raw image, the offset representing the difference between the intensity values for each pixel in the raw image and the desired intensity values for the pixel. The desired intensity values may be pre-defined color or RGB intensity values associated with the natural or a desired color of the various optical components or structure (e.g., retina, vitreous, lesions, etc.). The pre-defined intensity values may be stored as part of the instructions associated with the color-shift filtration module 134 in memory 121.

As an illustrative example, user input may provide color-shift information indicating that the patient has a yellow-tinted IOL, corresponding to a shade of yellow. In such an example, the color-shift filtration module 134 may then apply a filter to the raw image to adjust the RGB values of each pixel in the image by an offset corresponding to the shade of yellow. Subsequent to adjusting the RGB values of each of the pixels, a corrected image may be generated as if the patient's eye did not have a yellow-tinted IOL inserted in it.

In various embodiments, the user interface 125 may include a display showing one or more menu items for receiving color-shift information from a user. The user interface 125 may include a series of UI features to allow a practitioner to indicate the presence, color intensity, and other aspects of a color-shift in a raw image. For example, the user interface 125 may provide an option for the practitioner to indicate whether the patient has a nuclear sclerotic cataract or a yellow-tinted IOL.

In another example, the user interface 125 may provide a number of UI features (e.g., radio buttons) and associated rating scales (e.g., lens opacities classification (LOCS)) and/or visual color representations (e.g., images), to prompt practitioners to enter color-shift (e.g., yellow-shift) information. For example, the LOCS II and LOCS III rating scales, which are image-based rating scales, may be used. A degree of yellowing or yellow-shift may be associated with each of the various levels of the LOCS grading scale. As an example, a practitioner may view the raw image and determine that the degree of yellowing in the image corresponds to a certain color or grade of nuclear sclerotic cataract in the LOCS II system.

Alternatively, or additionally, images may be provided such that a practitioner may make a selection using visual matching of the images to a raw image or view of the patient's eye. As an example, multiple radio buttons with multiple corresponding sample images may be provided, such that, for example, a practitioner can look at the degree of yellowing in the raw image, visually match it to a sample image that reflects a similar degree of yellowing, and select a corresponding radio button. By providing a sample image and radio button selector for each level of the LOCS grading scale, a practitioner can quickly indicate the color and/or color intensity of the color-shift.

The UI features may also include radio buttons and associated images indicating one-plus (1+) nuclear sclerosis, two-plus (2+) nuclear sclerosis, three-plus (3+) nuclear sclerosis, and four-plus (4+) nuclear sclerosis. In another example, UI features, e.g., check box, for tinted Intra-Ocular Lenses (IOLs), or of IOLs with chromophores, may also be included, as well as a dropdown menu of individually named IOLs for which it would be desirable to have a filter for eliminating color-shift caused by the tint.

The information provided by the one or more menu selections of a user interface as described above is processed by the color-shift detection module 122 to determine how to color correct the raw image. For example, once the intensity, color, and/or shade of yellow associated with a nuclear sclerosis cataract or an IOL is determined, the color-shift detection module 122 may share such information as part of the color-shift information to the color-shift filtration module 134 to generate and apply a filter to correct for the color-shift in the raw image.

In addition or instead of receiving user input indicative of the color-shift information, the color-shift detection module 122 may also be configured to automatically determine the color-shift information by processing raw images received by the imager 102. For example, as discussed, the color-shift detection module 122 may comprise an image detection model configured to detect the presence of a structure in the raw image for which a natural color is known. By determining a difference between the color of the structure presented in the raw image and the known natural color of the structure, a color-shift for the image may be determined.

For example, a structure presented in the raw image may be an optic nerve head, which is known to have a natural white color. In such an example, the color-shift detection module 122 may use the image detection model to determine the location of the optic nerve head and the color of the optic nerve head in the raw image. The color-shift detection module 122 may then determine the difference between the color of the optic nerve head presented in the raw image and the natural, white color of the optic nerve head. Information indicative of the difference may then be shared as part of the color-shift information to the color-shift filtration module 134 to generate and apply a filter in order to correct for the color-shift in the raw image. A similar technique can be applied when using oxyhemoglobin and deoxyhemoglobin in retinal arteries and veins as reference structures.

The image detection model of the color-shift detection module 122 may require training using a training data set. The training data set may comprise information associated with a plurality of images, often hundreds, thousands, or more, that are manually labeled to reflect attributes, metadata, or other information about the image. For example, a set of hundreds or thousands of captured images including an optic nerve head may be manually labeled to indicate the location of the optic nerve head (e.g., pixel information associated with the optic nerve head). A model is then "trained" by using a machine learning algorithm to reduce error in predictions about the location of the optic nerve head until the error is reduced to a negligible amount.

Once the location of the optic nerve head is determined, the color-shift detection module may measure a set of color intensities (e.g., RGB values) for each pixel associated with the optic nerve head. The color-shift detection module may then determine a difference between the measured color intensities and a set of known color intensities for an optic nerve head to determine the presence of an illuminant causing a color-shift. Therefore, in response to receiving the color-shift information from the color-shift detection module 122, whether as a result of user input or through image detection, the color-shift filtration module may generate a color correction filter using the color-shift information. The color correction filter, when applied to the raw image, may be used to generate a corrected image with some or all of the color-shift appearing in the raw image eliminated. Similar techniques for training an image detection model can be applied when using oxyhemoglobin and deoxyhemoglobin in retinal arteries and veins as reference structures.

Figure 2:
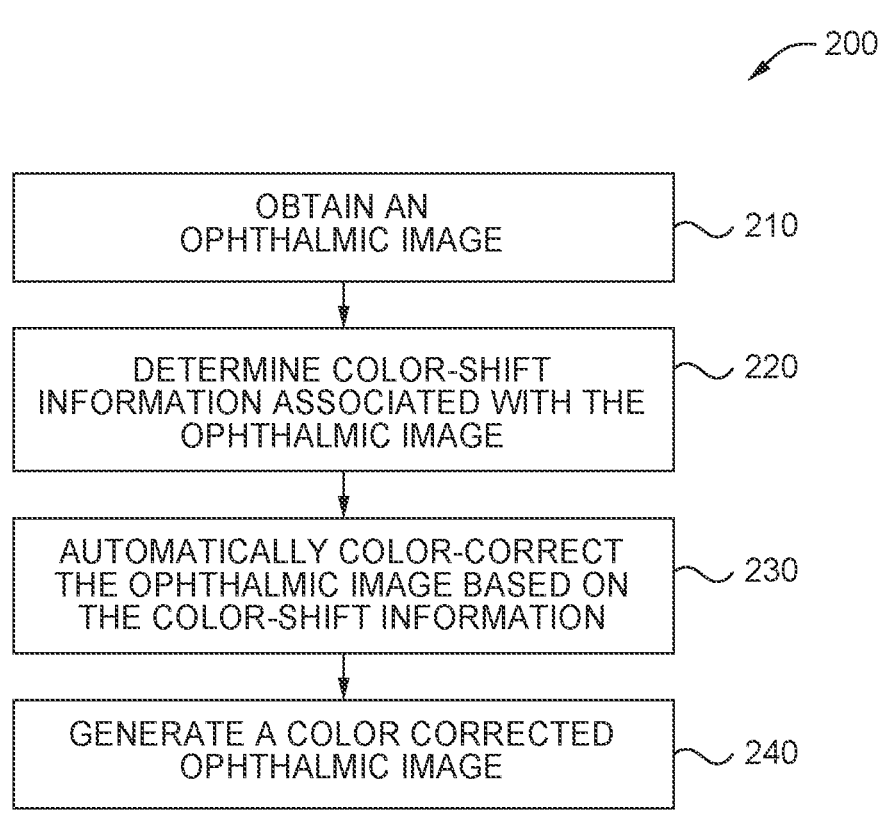
FIG. 2 is a flowchart of a method of providing color-corrected ophthalmic images, according to certain embodiments.

FIG. 2 is a flowchart of a method 200 performed by an ophthalmic system ("system"). In certain embodiments, the system is or comprises the imaging device 104 of FIG. 1, with an imager 102 incorporated therein. In certain embodiments, the system comprises a computing device that is in communication with an imager, such as imager 102.

At block 210, the system obtains an ophthalmic image (also referred to as a "raw image"), such as a retinal image. The ophthalmic image may be a digital retinal image, multi-spectral image, or high-spectral image, or a similar ophthalmic image. The image may have a color shift, such that the color appearance of various optical components, e.g., the vitreous and the retina, may be altered due to the presence of a nuclear sclerotic cataract, a yellow tinted intraocular lens ("IOL"), or for some other reason. The image may be captured by an imager that is part of the system or an imager that is in communication with the system over a wired or wireless network.

At block 220, the system determines color-shift information associated with the obtained image. As described above, the system may determine color-shift information based on user input and/or by processing and analyzing the obtained image. The color-shift information indicates how or to what extent color in the obtained image can be corrected to at least partially remove or remedy the effect of, for example, a nuclear sclerotic cataract or a yellow-tinted IOL on the color of the obtained image. Color-shift information input by a user may indicate one or more of: a color of the patient's nuclear sclerotic cataract, the type and/or color of an IOL in the lens capsule, observed color of the obtained image, etc., as described above. Color-shift information derived automatically (e.g., without user input) by processing the obtained image may indicate the color of the obtained image, such as intensity values (e.g., red, green, blue (RGB) values) associated with one or more pixels in the obtained image. In certain embodiments, the system may determine color-shift information based on user input as well as automatically processing the obtained image as described above.

At block 230, the system automatically color corrects the obtained image based on the color-shift information. A variety of techniques may be used to color correct the obtained image based on the determined color-shift information. As an example, a filter may be generated based on the color-shift information and then applied to the obtained image to correct the color-shift in the obtained image, resulting in a corrected image with the desired or target color intensity. Additional information about how a filter can be generated and applied to the obtained image was provided above and is omitted here for brevity.

At block 240, the system generates a color corrected image. For example, the system may generate and display the color corrected image using a display that is a part of the system, further process color corrected image, and/or transmit the color corrected image to another display or system, over a wired or wireless network, for displaying to a clinician and/or further processing. An example of further processing may include additional image detection techniques and/or other types of processing performed to derive information that can be used for actionable information or guidance to a clinician. As discussed, correcting the color of the obtained image prior to the additional processing is advantageous because the additional processing may be performed by artificial intelligence models that are trained using images that are not color-shifted and may, therefore, make inaccurate predictions when the input to such models is a color-shifted image.

It will be appreciated that the elements and the configuration shown in FIG. 2 are exemplary in nature only, and that various elements could be added or omitted, or otherwise configured or arranged for various applications without departing from the scope of this disclosure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of generating a color-corrected ophthalmic image, the method comprising:
   obtaining an ophthalmic image of an eye with a tinted intraocular lens ("IOL") implanted therein;

determining color-shift information associated with the ophthalmic image based on at least one of user input and processing the obtained image, the color-shift information being indicative of an extent to which color in at least one portion of the obtained image is to be corrected to at least partially remedy an effect of the tinted IOL on the color in the at least one portion of the obtained image;

color-correcting the ophthalmic image based on the color-shift information; and generating the color-corrected ophthalmic image based on the color-correcting.

2. The method of claim 1, wherein determining the color-shift information is based on the user input.

3. The method of claim 2, wherein the user input indicates one or more of: a type of the IOL, a color of the IOL, and an observed color of the obtained image.

4. The method of claim 2, wherein:
   the user input includes a selection of a sample image corresponding to a type and/or color of the IOL, and
   the selection is based on a user visually matching the color of the IOL in the obtained image and the sample image.

5. The method of claim 1, wherein determining the color-shift information comprises:
   automatically determining a location of a structure of the eye in the obtained image; and
   measuring a difference in a color of the structure as the structure appears in the obtained image and a defined color associated with the structure.

6. The method of claim 5, wherein the measuring comprises:
   determining color intensity values of one or more pixels associated with the structure in the obtained image; and
   determining an offset between the color intensity values of the one or more pixels and pre-defined color intensity values for the structure, and wherein the offset is representative of the difference.

7. The method of claim 1, wherein color-correcting the ophthalmic image comprises:
   generating a filter based on the color-shift information; and
   applying the filter to the obtained image.

8. The method of claim 7, wherein the filter is representative of an offset corresponding to a difference between intensity values for each pixel in the obtained image and pre-defined intensity values for the pixel.

9. The method of claim 1, wherein color-correcting the ophthalmic image comprises:
   adjusting intensity values of one or more pixels in the obtained image to achieve pre-defined RGB (Red, Green, Blue) values for the one or more pixels.

10. An ophthalmic imaging device, comprising:
   an imager configured to obtain an ophthalmic image of an eye with a tinted intraocular lens ("IOL") implanted therein;
   one or more memories configured to store executable instructions;
   one or more processors in data communication with the one or more memories and configured to execute the instructions to:
      determine color-shift information associated with the ophthalmic image based on at least one of user input and by processing the obtained image, the color-shift information indicative of the extent to which color in the obtained image is to be corrected to at least partially remedy the effect of the tinted IOL on the color of the obtained image;

color-correct the ophthalmic image based on the color-shift information; and generate the color-corrected ophthalmic image based on the color-correcting.

11. The ophthalmic imaging device of claim 10, wherein the one or more processors being configured to determine the color-shift information comprises the one or more processors being configured to determine the color-shift information based on user input.

12. The ophthalmic imaging device of claim 11, wherein the user input indicates one or more of: a type of the IOL, a color of the IOL, an observed color of the obtained image.

13. The ophthalmic imaging device of claim 11, wherein:

the user input includes a selection of a sample image corresponding to a type and/or color of the IOL, and the selection is based on a user visually matching the color of the IOL in the obtained image and the sample image.

14. The ophthalmic imaging device of claim 10, wherein the one or more processors being configured to determine the color-shift information comprises the one or more processors being configured to:

automatically determine a location of a structure of the eye in the obtained image; and measure a difference in a color of the structure as the structure appears in the obtained image and a defined color associated with the structure.

* * * * *